United States Patent [19]

Radford et al.

[11] Patent Number: 5,637,303
[45] Date of Patent: Jun. 10, 1997

[54] USE OF A PHOSPHOLIPASE D MUTANT OF *CORYNEBACTERIUM PSEUDOTUBERCULOSIS* FOR VACCINATION

[75] Inventors: Anthony J. Radford, Kew; Adrian L. M. Hodgson, East Malvern, both of Australia

[73] Assignee: Commonwealth Scientific and Industrial Research Organisation, Australia

[21] Appl. No.: 416,463

[22] Filed: Apr. 4, 1995

Related U.S. Application Data

[63] Continuation of Ser. No. 39,237, filed as PCT/AU91/00471, Oct. 14, 1991, and published as WO92/07582, May 14, 1992, abandoned.

[30] Foreign Application Priority Data

Oct. 25, 1990 [AU] Australia .................. PK3005/90

[51] Int. Cl.$^6$ .................................................. A61K 39/05
[52] U.S. Cl. .................. 424/245.1; 424/93.2; 424/9.34; 424/200.1; 424/235.1; 424/282.1; 424/823; 424/824
[58] Field of Search .................. 424/93.2, 93.4, 424/245.1, 823, 824, 200.1, 235.1, 282.1

[56] References Cited

U.S. PATENT DOCUMENTS 3,853,990  12/1974  Madigan et al. .
4,925,792   5/1990  Rappuoli .
5,085,862   2/1992  Klein et al. .

FOREIGN PATENT DOCUMENTS

| 74599/87 | 1/1988 | Australia . |
|---|---|---|
| 19550/88 | 12/1988 | Australia . |
| 38677/89 | 1/1990 | Australia . |
| 52626/90 | 9/1990 | Australia . |
| 52392/90 | 10/1990 | Australia . |
| 9010701 | 9/1990 | WIPO . |
| 9011351 | 10/1990 | WIPO . |

OTHER PUBLICATIONS

Lea Master et al. Am. J. Vet. Res. 48(5):869–72 (see abstract) 1987.
Cameron et al. Onderstepoort J. Vet. Res. 39(1):11–24 1972 (see abstract).
Feinberg et al., *Analytical Biochemistry*, 132, 6–13, 1983.
Hodgson et al., *Nucleic Acids Research*, 18, 7, 1891, 1990.
Hodgson et al., *Journal of Bacteriology*, 172, 3, 1256–1261, 1990.

*Primary Examiner*—Anthony C. Caputa
*Attorney, Agent, or Firm*—Bacon & Thomas

[57] ABSTRACT

The present invention relates to a vaccine vector comprising a virulent corynebacterium or related organism which is incapable of expressing an active virulent factor or a non-virulent corynebacterium or related organism which synthesises an immuno protection effective amount of an antigen of a pathogenic organism and its use to stimulate a protective immune response against virulent members of this group.

3 Claims, 6 Drawing Sheets

```
5' TTGTTATAGC GCGAGGTGGG GCCTAAAAGC CACGTTATAA AATCCTTCAT CTGTCTTTGA   60
   TGCAGCGTCC CTGATCGCGT TGCTGTCGAC GATGCTCCGC ATCCCTGCA TCTGTACCGG  120
                          Sal I
   GTCTTTCCTG TGGACGTTTT TGCCGTTCTT TTTTAGGAGA TTGCCGCAGA CGTTGCAGTG  180
   ATTCCGGTAT GGATGTGAAG CCATAATCAA TAATTAGCAG CTTTAAATCT GCTATGGATA  240
   CCCTAAAAGT TACAATTTTG GACACATTTG TTGTCCTTTA AGTTCAAAAA CCTTGAACGT  300
   ATCTGACGCA TTTGAATACA TATCATTCAT ATGTAATGCC TGATTGATAA CGCCAACCTT  360
   TTAAATGGGG CTCCCGCTCT CCTCTCTAGG GGATGGGTTTT CTGTGT CAAC TGTCA      410
```

Fig.3C.

USE OF A PHOSPHOLIPASE D MUTANT OF *CORYNEBACTERIUM PSEUDOTUBERCULOSIS* FOR VACCINATION

This application is a Continuation of application Ser. No. 08/039,237, filed Jun. 18, 1993, now abandoned, which is the national phase of PCT/AU91/00471, filed Oct. 14, 1991 and published as WO92/07582 May 14, 1992.

The present invention relates generally to the use of corynebacteria and related organisms and/or mutants or derivatives thereof as vaccine vectors.

An animal pathogen of importance to the livestock industry is *Corynebacterium pseudotuberculosis*, which is the causative agent of caseous lymphadenitis (CLA), commonly known as "cheesy gland". This disease affects mainly sheep and goats but can also affect horses.

The major virulence factor of *C. pseudotuberculosis* appears to be a 31 kDa exotoxin called phospholipase D (PLD). Sheep can be protected from CLA by vaccination with a formalin-treated precipitate of *C. pseudotuberculosis* culture supernatant or using a toxoid form of pure PLD.

In work leading up to the present invention, it was sought to utilise the adjuvant properties associated with corynebacteria and related organisms to produce vaccine vectors capable of stimulating a protective immune response against virulent members of this group. This is achieved by deleting virulence genes from selected species or employing non-pathogenic or avirulent species manipulated to express appropriate antigenic material, such as a recombinant toxoid.

Accordingly, one aspect of the present invention relates to a vaccine vector comprising a Corynebacterium or related organism which is incapable of expressing an active virulence factor or which synthesises an immunoprotection effective amount of an antigen from a pathogenic organism.

The term "vaccine vector" is used in its widest sense to include a biological means for antigen presentation. The biological means is conveniently a microorganism and is generally viable although dead organisms could be employed. The biological vector is non-pathogenic or rendered avirulent or is given in non-pathogenic or avirulent effective amounts. By "antigen presentation" means expression of naturally occurring antigens and/or expression of recombinant antigens such as by transforming the biological vector with a plasmid carrying a gene or genes encoding the antigen or antigenic parts thereof and which is then expressed; or where the plasmid and/or gene or genes and/or parts thereof are integrated into the host genome, which includes the chromosome and/or any naturally or non-naturally occurring extra-chromosomal element, wherein the gene or genes or parts thereof are expressed. Alternatively, the biological vector is manipulated to prevent or reduce expression of an antigen, such as a virulence factor, or to produce an altered and non-toxic form of the antigen or parts thereof. In this case, the biological vector presents other non-toxic antigens or toxic antigens in non-virulence or non-pathogenic effective amounts. In any event, the cell or gene or both may need to be further manipulated to ensure the antigen is secreted in sufficient amounts. In one embodiment, the antigen expressed is recombinant and, if it is itself a virulence factor, the recombinant antigen will also be de-toxified.

The present invention is described using, as a vaccine vector, *C. pseudotuberculosis* carrying a deletion in the gene encoding PLD which, up to the present time, provides the best model of the subject invention. However, one skilled in the art will readily appreciate the applicability of the present invention to other species of Corynebacterium and other related organisms such as species of Brevibacterium. Furthermore, the present invention extends to any single or multiple nucleotide substitution, addition and/or deletion in the virulence gene which results in the inactivation of that gene or which results in an avirulent form of product, such as an inactive toxin.

In accordance with the present invention, a vaccine vector strain of *C. pseudotuberculosis* was obtained by genetically disrupting the PLD gene from a virulent strain using recombinant techniques as herein described in the Examples. It is to be appreciated, however, that other techniques such as chemical- or radiation-induced mutagenesis could also be employed without departing from the scope of the present invention.

Briefly, the PLD gene was disrupted by deletion and an erythromycin resistance gene inserted within the gene. This was transferred into a virulent *C. pseudotuberculosis* on a shuttle vector such as a pEP vector bearing a kanamycin resistance determinant (see Australian Patent Application No. PJ8815/90). A variant pEP vector carrying a different antibiotic resistance marker was then also introduced into the bacteria and selection applied for the second plasmid. This encouraged the recombination of the deleted gene into the chromosomal PLD gene, thus conferring erythromycin resistance on the strain and eliminating PLD production. Selection for the second pEP plasmid acts against maintenance of the first plasmid carrying the mutant PLD. The first plasmid will be lost, but in some cases, recombination of the mutant PLD and erythromycin resistance gene to the chromosome will have occurred. As PLD mediates clearing on blood plates, the loss of the clearing phenotype with the concomitant loss of kanamycin resistance and maintenance of erythromycin resistance indicates incorporation of the deleted gene into the chromosome of *C. pseudotuberculosis*.

The use of deletion mutants is particularly useful since these are incapable of reversion to the wild type (virulent) phenotype. The combined effect of the adjuvant properties associated with Corynebacterium and the rendering of a virulent strain avirulent, make this a particularly potent vaccine vector, capable of stimulating an immunoprotective effect amount of antibody and/or other immune protective factors (including cells) against the virulent organism.

Accordingly, this aspect of the present invention relates to a vaccine vector comprising *C. pseudotuberculosis* carrying a single or multiple nucleotide substitution, addition and/or deletion in the gene encoding PLD. The substitution, addition and/or deletion in the PLD gene must be effective to prevent expression of the gene altogether, to prevent synthesis of active PLD or to result in only a non-virulent effective amount of PLD being synthesized. The vaccine will generally consist of a biological pure formulation of the organism and may additionally comprise one or more pharmaceutically acceptable carriers and/or diluents depending on the intended recipient and mode of administration.

Another aspect of the present invention contemplates a method for vaccinating a livestock animal against CLA and/or treating an animal infected with *C. pseudotuberculosis* which method comprises administering to said animal an immunoprotective amount of a derivative of *C. pseudotuberculosis* carrying a single or multiple nucleotide substitution, addition and/or deletion in the gene encoding PLD for a time and under conditions sufficient to render the animal immunoresponsive to current or subsequent *C. pseudotuberculosis* infection.

Administration may be by any suitable route such as by oral or intravenous administration. The preparation may also be in dry or liquid form. The route of administration chosen may also necessitate additional components such as protease inhibitors and the like.

In yet another aspect of the present invention, there is provided a method for the production of non-active or toxoid PLD, which method comprises culturing C. pseudotuberculosis carrying a single or multiple nucleotide substitution, addition and/or deletion in the gene encoding PLD, and recovering non-active or toxoided PLD produced by expression of said gene. The non-active or toxoided PLD produced by this method may, for example, be used as the active immunogen in a vaccine for stimulating a protective immune response against C. pseudotuberculosis.

The applicability of the present invention to other organisms as disease treatments is readily identifiable. For example, a gene encoding a virulent factor, such as PLD, can be mutated in vitro or in vivo by one or more insertion, deletion and/or substitution mutations so as to encode toxoid and then introduced into a suitable corynebacterium or related organism to produce a vaccine vector. Alternatively, the virulent factor-encoding gene may be deleted or otherwise disrupted in a corynebacterium or related organism to obtain an avirulent vaccine vector. All such embodiments are included within the scope of the present invention.

The present invention is further described by reference to the following non-limiting Figures and Examples:

In the Figures:

FIG. 1 is a pictorial representation of a site-specific recombination plasmid. The PLD gene was sub-cloned as a 1.5 kb SacI fragment into the PstI site of pEP2. The erythromycin-resistance gene was then cloned as a 1.7 kb HindIII fragment into the PstI site of the PLD gene thereby creating a deletion.

FIG. 2 is a photographic representation depicting mutagenesis of the C. pseudotuberculosis PLD gene. Wild-type C. pseudotuberculosis were mutated using site-specific recombination. Cells were plated onto sheep blood plates. Greater than 90% of mutated cells failed to cause erythrocyte lysis suggesting that the PLD gene had been inactivated.

FIGS. 3(A) and (B) is a photographic representation showing Southern blot analyses of C. pseudotuberculosis mutants. Panel A. SacI digested genomic DNA hybridised with a PLD-specific probe. Lanes: A, wild-type C. pseudotuberculosis strain 231; B, strain 231 containing recombination plasmid pBTB58; C, mutant 1; D, mutant 2; E, mutant 3; F, as lane B but DNA undigested; G, DNA from C. pseudotuberculosis retaining PLD activity after mutagenesis. Higher molecular weight and ghost bands are probably partially digested material. Panel B. As Panel A but filter hybridised with an erythromycin gene-specific probe. Note absence of the 2.0 kb PLD gene SacI fragment in Lanes A and B.

FIG. 3(C) is a pictorial representation showing the nucleotide sequence of the 5' (SEQ ID No. 1) and 3' (SEQ ID No. 2) regions of C. pseudotuberculosis phospholipase D gene. Boxed regions show overlaps with the published sequence; dots below STOP indicate putative translational terminator; inverted arrows define transcriptional terminator stem (S) and dotted line the loop (L) structure (−13.6 kcal).

EXAMPLE 1

MATERIALS AND METHODS

Figure 1:
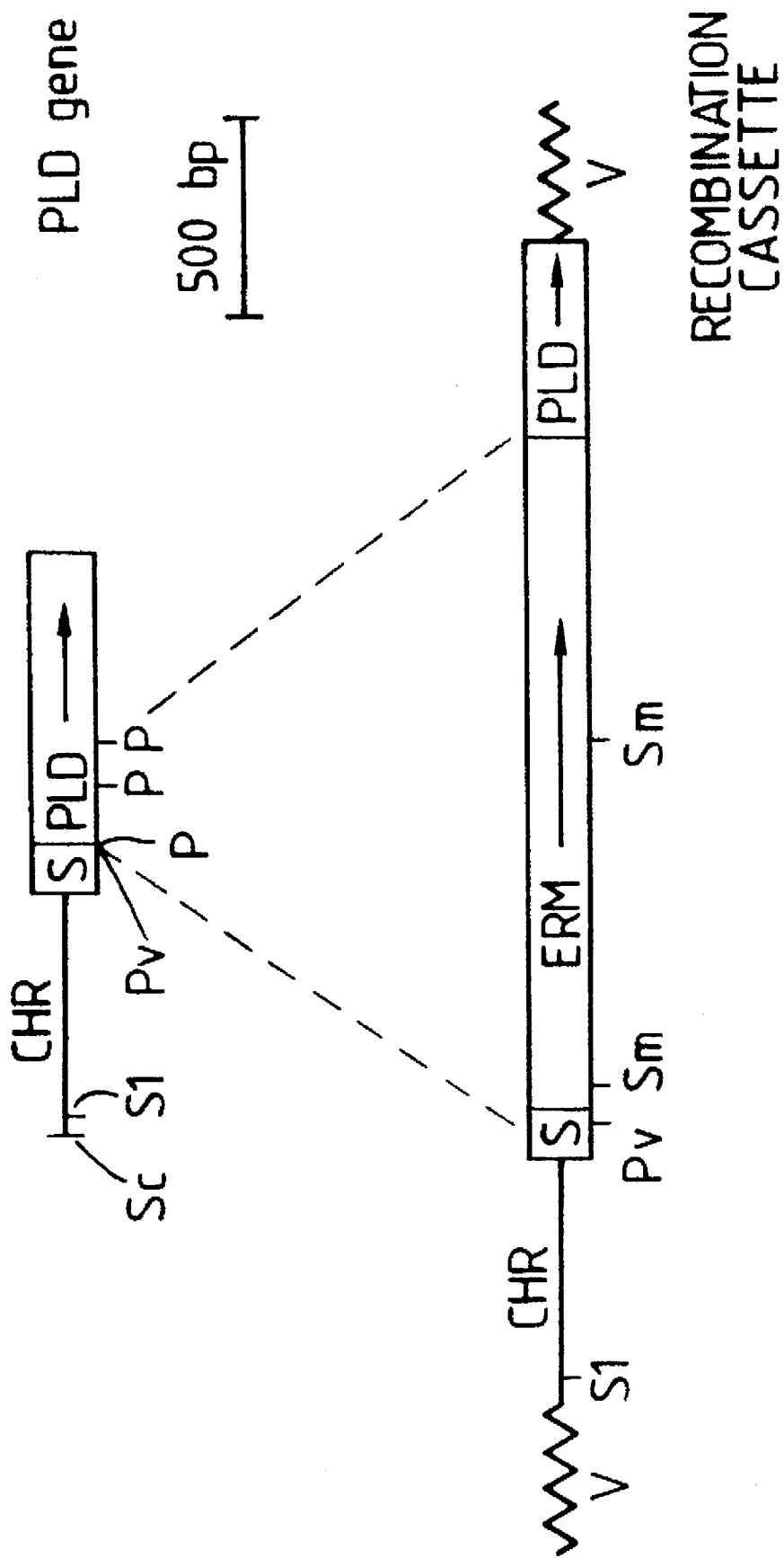

Bacterial strains and plasmids.

E. coli strain DH5alpha (BRL) was host for a pUC118 clone of a Corynebacterium erythromycin resistance gene (Hodgson et al 1990b) and the E. coli-Mycobacterium-Corynebacterium shuttle plasmids pEP2 and pEP3 (Radford and Hodgson, submitted for publication). The C. pseudotuberculosis strain wild-type for PLD production was obtained from Dr Doug Burrell (CSIRO Division of Animal Health, Amidale, NSW). Rhodococcus equi strain CC50 was a gift from Dr Keith Hughes (Melbourne University, Department of Veterinary Science, Werribee).

Media.

Transformed E. coli were grown in Luria broth (LB: 10 g tryprone, 5 g yeast extract, 10 g NaCl per liter) containing 50 µg ampicillin (Sigma), 50 µg kanamycin sulphate (Boehringer Mannheim), 100 µg erythromycin (Boehringer Mannheim) or 150 µg hygromycin B (Sigma) per ml as necessary. Cells of C. pseudotuberculosis were cultured at 37° C. in brain heart infusion media (Difco) containing 0.1% v/v Tween 80 (BHI) at 37° C. Transformed cells were selected on BHI supplemented with 50 µg kanamycin, 150 µg hygromycin B or 100 µg erythromycin per ml. Putative C. pseudotuberculosis mutants were selected on BHI containing 100 ng erythromycin and 150 µg hygromycin B (Sigma) per ml. To detect PLD activity, C. pseudotuberculosis cells were cultured on sheep blood plates (LB containing 5% v/v defribinated whole sheep blood, 10% v/v filtered (0.2 µm) culture supernatant from Rhodococcus equi.

DNA techniques.

All DNA manipulations were conducted using standard protocols (Sambrook et al., 1990). Genomic DNA was isolated from C. pseudotuberculosis as described previously (Hodgson et al., 1990a and Radford and Hodgson, submitted for publication).

Construction of a recombinant plasmid.

A recombinant plasmid was constructed by cloning a fragment carrying the PLD gene into the PstI site of pEP2 (pBTB58). A 1.7 kb HindIII fragment containing an erythromycin resistance gene was cloned into the PLD gene deleted with PstI (pBTB58). The orientation of the PLD and erythromycin genes was determined by SalI restriction analysis.

Mutagenesis of the C. pseudotuberculosis PLD gene.

The recombination plasmid was electroporated into wild-type C. pseudotuberculosis and transformants were selected on BHI containing erythromycin and kanamycin. Cells of C. pseudotuberculosis harbouring the recombination plasmid were then electroporated with pEP3 and the transformants selected on BHI plates supplemented with erythromycin, kanamycin and hygromycin B. The presence of plasmid pEP3 was confirmed using Southern blot analysis. A transformant containing both plasmids was grown overnight in BHI containing all three drugs. The culture was sub-cultured 1:100 in BHI broth supplemented with only hygromycin B and shaken overnight. The sub-culturing regime was repeated a total of three times. The final broth culture was dilution plated onto sheep blood plates supplemented with erythromycin and hygromycin B. Single colonies were patched to BHI plates containing erythromycin and hygromycin B and only kanamycin.

Examination of mutated C. pseudotuberculosis for PLD activity.

Three mutated C. pseudotuberculosis strains and the wild-type strain were grown for 2 days in BHI, pelleted, resuspended in 100 µl of phosphate buffered saline (PBS) then sonicated to release cellular protein. Samples (10 µl) were spotted onto sheep blood plates and held at 37° C. overnight.

Plasmid curing.

A hygromycin B and erythromycin resistant derivative of C. pseudotuberculosis unable to produce zones of lysis on sheep blood plates (tox-minus), was streaked for single colonies onto plain BHI plates. Cells from the outer margin from a single colony were streaked in the same way. The process was repeated a total of five times. A single colony from the fifth subculture was plated onto BHI supplemented with either hygromycin B or erythromycin.

DNA analysis of C, pseudotuberculosis mutants

Total genomic DNA was isolated from three Toxminus C. pseudotuberculosis colonies. DNA was digested using SacI, electrophoresed and Southern blotted to Zeta-Probe nylon filters (Bio-Rad). Filters were hybridised overnight at 37° C. with a PLD gene-specific probe, labelled with $^{32}$P using random primers (Feinberg and Vogelstein, 1983), then washed at increasing stringency as necessary (up to 65° C. in 0.2×SSC) and exposed to X-ray film (Fuji RX). Wild-type C. pseudotuberculosis and those transformed with pBTB58 were included as controls. Filters were held in 0.4M NaOH at 45° C. for 30 min., washed in 0.1×SSC, 0.1% (w/v) SDS, 0.2M tris HCl pH 7.5 at 45° C. for 30 min then hybridised with an erythromycin gene-specific probe, washed and exposed to X-ray film as described above.

PLD gene expression in Toxminus C. pseudotuberculosis.

Plasmid pBTB50 containing the wild-type PLD gene was electroporated into a Toxminus C. pseudotuberculosis. Transformants were serially diluted and plated onto sheep-blood plates containing kanamycin. Zones of erythrocyte lysis produced by wild-type and transformed Toxminus cells were measured.

EXAMPLE 2

MUTAGENESIS OF THE C. Pseudotuberculosis PLD GENE

Figure 2:
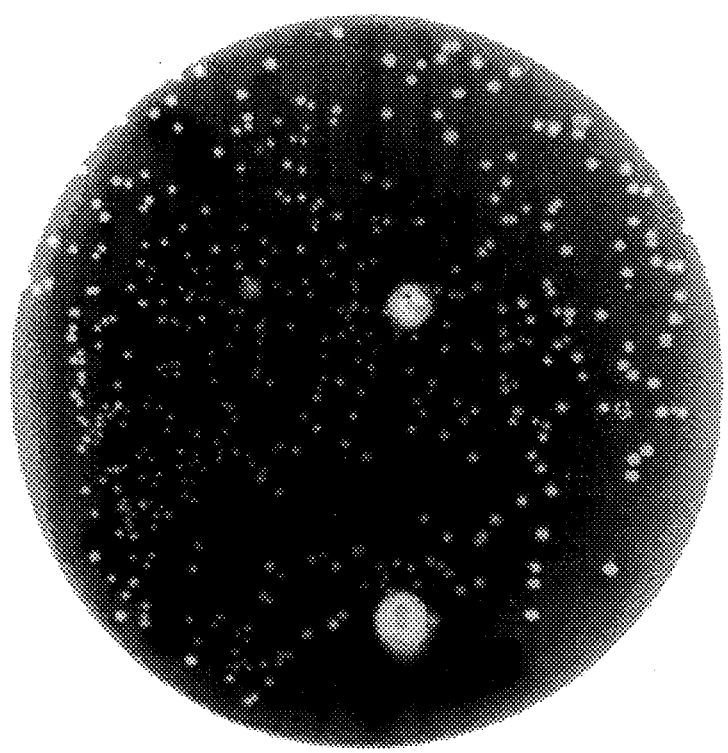

To make a vector capable of site-specific recombination with the C. pseudotuberculosis chromosome, the PLD gene was first sub-cloned into the pEP2 shuttle vector. The PLD gene was then deleted with PstI and an erythromycin-resistance gene was introduced into the PstI site to produce plasmid pBTB58 (FIG. 1). Wild-type C. pseudotuberculosis were transformed with pBTB58 and subsequently with the hygromycin resistance shuttle plasmid pEP3. Cells transformed with both plasmids were selected on media containing kanamycin, erythromycin and hygromycin. In order to maintain plasmid pEP3 and promote the loss of plasmid pBTB58 through plasmid segregation, cells containing both plasmids were subcultured to media containing only hygromycin. To detect those cells in which a recombination event had occurred, cultures were plated onto blood plates containing both hygromycin and erythromycin. Greater than 90% of the hygromycin and erythromycin resistant colonies failed to produce zones of lysis on blood plates (FIG. 2). Furthermore, all 10 of the colonies producing zones spotted were resistant to kanamycin whereas 50 zoneless mutants examined were all kanamycin sensitive. These results suggest that plasmid pBTB58 was lost from the host cell and that a double crossover recombination event had introduced the erythromycin resistance gene into the chromosome inactivating the PLD gene. Colonies resistant to all three antibiotics and able to produce zones on blood plates could either be the result of a single crossover event with the chromosome or represent cells in which both pEP3 and pBTB58 had been maintained. To confirm that the mutated bacteria were not producing PLD, cell lysates were spotted onto blood plates. Only cellular protein obtained from the parental C. pseudotuberculosis produced a zone of erythrocyte lysis. This result suggests that the mutants are incapable of producing zones of lysis on sheep blood plates because they do not produce PLD and not because they produce a non-secreted mutated PLD protein.

Figure 3A:
Figure 3B:

To confirm that the predicted recombination event with the C. pseudotuberculosis chromosome had occurred, total DNA isolated from three Toxminus, one variant capable of producing zones after mutagenesis, the wild-type bacterium harbouring pBTB58 and the wild-type strain was examined using Southern blot analysis (FIG. 3). When the wild-type C. pseudotuberculosis genome cut with SacI was probed using the PLD gene a single 2.0 kb band was observed (FIG. 3A). Genomic DNA isolated from three Toxminus bacteria analysed in the same way showed only a single band of 3.4 kb (FIG. 3A). This result is consistent with the occurrence of a double crossover event resulting in the replacement of the chromosomal PLD gene with the deleted PLD/erythromycin resistance gene cassette.

When uncut genomic DNA isolated from a variant able to lyse sheep blood plates even after mutagenesis was probed using the PLD gene probe, a band pattern identical to that produced by the pBTB58 control was observed. This result suggests that the ability to lyse sheep blood was retained because pBTB58 had not been lost from the cell and the PLD gene had not been mutated.

When the same filter was subsequently probed with an erythromycin resistance gene-specific probe only the 3.4 kb SacI fragment hybridised (FIG. 3B) this confirms that the erythromycin gene had been incorporated into the PLD gene.

Expression of the PLD gene in Toxminus C. pseudotuberculosis.

Plasmid pEP2 carrying the PLD gene was electroporated into Toxminus C. pseudotuberculosis. To detect PLD activity, transformants were plated onto blood plates. Transformed cells produced zones of lysis. This result suggests that the cloned PLD gene is expressed in the C. pseudotuberculosis mutant and that its product is secreted from the host cell.

A second PLD negative strain of C. pseudotuberculosis (Toxminus II) was generated in the same way as for Toxminus except: (1) a different cloned fragment of the PLD gene was used to create the recombinant cassette and (2) the erythromycin gene was cloned into the PLD PstI site in the opposite direction with respect to the PLD gene shown in FIG. 1.

The PLD gene was cloned as a 2.1 kb SacI fragment into the SacI site of pUC118 and the new sequence determined (FIG. 3C). A major feature of the second PLD gene clone is the presence of a putative transcriptional terminator just downstream of the translational stop codon (FIG. 3C). As with Toxminus, insertion of the erythromycin gene into the chromosomal PLD gene was confirmed by Southern blot analysis (data not shown). Toxminus II differs from Toxminus in that the erythromycin resistance gene is inserted into the chromosome in opposite orientations.

EXAMPLE 3

IMMUNOLOGICAL RESPONSE TO PLD NEGATIVE C. Pseudotuberculosis

Unshorn 9 month old sheep were inoculated with virulent PLD positive and PLD deleted C. pseudotuberculosis. Strain 231 is a high PLD producer, and 137e a low PLD producer, but both are pathogenic. Blood samples were taken on a weekly basis. Serological conversion was monitored using an enzyme immunoassay (EIA), where trays were coated with *C. pseudotuberculosis* 231 sonicate.

T cell response was measured by quantifying the release of gamma-interferon in a whole blood culture incubated with 5 µg per ml of the *C. pseudotuberculosis* sonicate. Levels of interferon were assayed using a capture-tag EIA.

Figure 4:
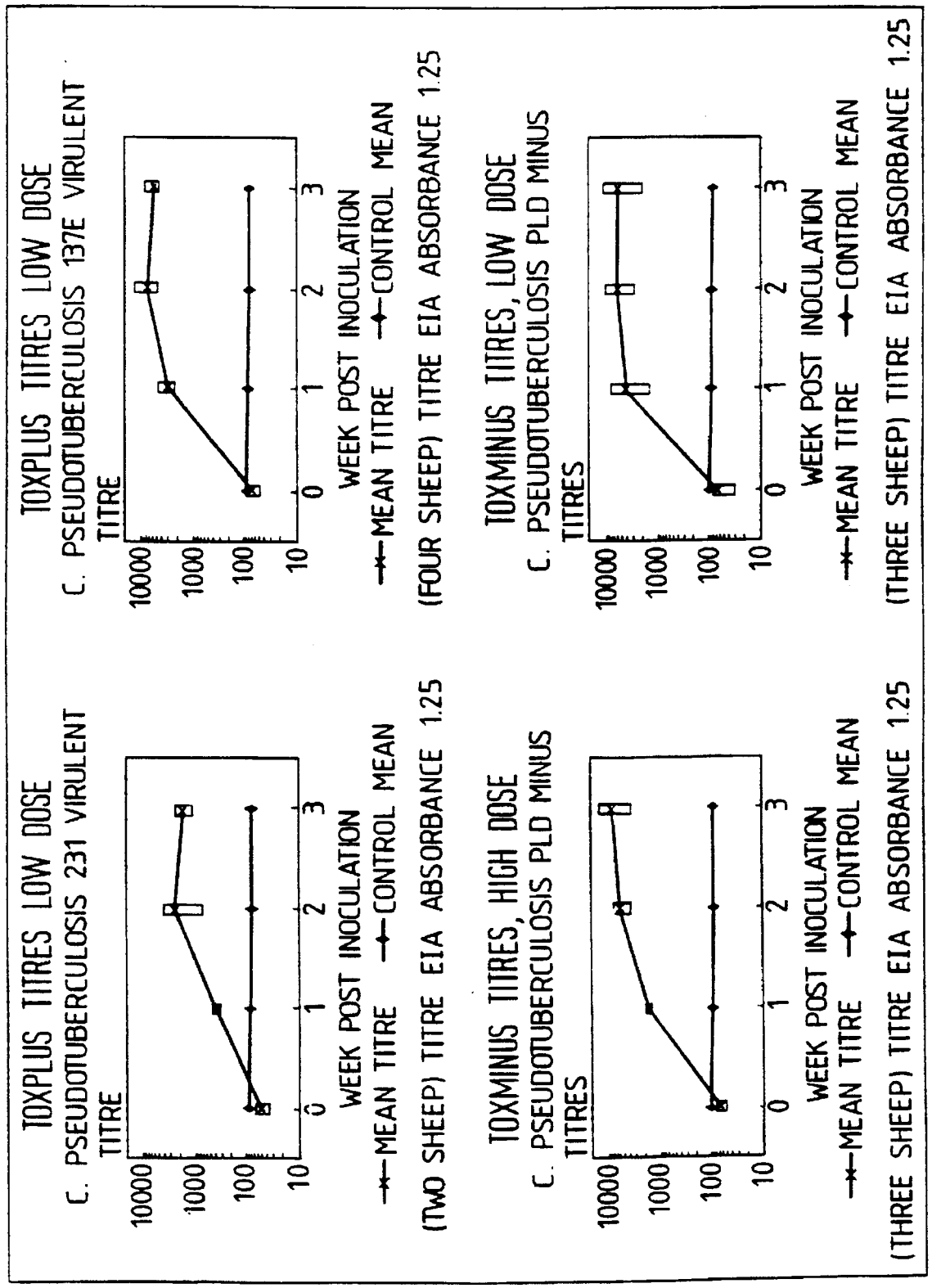
FIG. 4 is a graphical representation of the T cell responses of sheep injected with PLD-producing and Toxminus strains of C. pseudotuberculosis.

The results indicate a significant antibody response (Table 1) to the Toxminus *C. pseudotuberculosis* strain, and also marked T cell responses (FIG. 4). In both areas these are comparable to reactions stimulated by the parent virulent strain.

TABLE 1

CORYNEBACTERIUM PSEUDOTUBERCULOSIS VACCINATION
Virulent and Toxminus Strains, EIA Titres

| STRAIN CFU | PREBLEED 10/9/90 | 17/9/90 | 24/9/90 | 1/10/90 |
|---|---|---|---|---|
| Virulent 231 × $10^6$ | 38 | 340 | 440 | 2450 |
|  | 68 | 475 | 750 | 1150 |
| Virulent 137E × $10^8$ | 105 | 2400 | 5100 | 5400 |
|  | 48 | 3300 | 6800 | 4650 |
|  | 34 | 5000 | 14500 | 9000 |
|  | 108 | 2400 | 6100 | 5150 |
| Toxminus × $10^8$ | 82 | 1400 | 2700 | 1900 |
|  | 56 | 7800 | 10000 | 11000 |
|  | 52 | 2800 | 4300 | 4100 |
| Toxminus × $10^{10}$ | 80 | 1600 | 5800 | 14000 |
|  | 50 | 1700 | 3550 | 3400 |
|  | 60 | 1800 | 7800 | 7200 |
| Control | 115 | 80 | 70 | 64 |
|  | 76 | 96 | 90 | 90 |

Serological titres of vaccinated sheep. Titre is the inverse of the last dilution giving an absorbance>1.25 using strain 231 sonicate as coating antigen in an indirect EIA.

EXAMPLE 4

IMMUNOLOGICAL RESPONSE AND PROTECTION AGAINST CASEOUS LYMPHADENITIS IN SHEEP

To further assess both the efficacy and pathogenicity of the *C. pseudotuberculosis* Toxminus strain sheep were vaccinated with varying doses of *C. pseudotuberculosis* Toxminus intradermally into the skin 3 cm above the coronet of the left hind leg, and later challenged with virulent $4×10^6$ *C. pseudotuberculosis* strain 231 inoculated into the same site on the right hind leg. Five nine month old sheep were used for each vaccine doosage, and seven control sheep were challenged without vaccination (Table 2). Challenge was delivered 9 weeks following the vaccine doses, and protection was assessed a further 9 weeks later. Protection was assessed by examination of pathology at the site of challenge and at the popliteal lymph nodes, and culture of organisms from these sites. All sheep were autopsied and tissues examined for pathological signs. Sera was removed weekly and tested for *C. pseudotuberculosis* specific antibody by EIA.

TABLE 2

Initial Vaccination

| | Organism and dose *C. pseudotuberculosis* Strain Toxminus | | |
|---|---|---|---|
| No Sheep | Control | $2 × 10^7$ | $2 × 10^5$ |
| 5 | | X | |
| 5 | | | X |
| 7 | X | | |

Figure 5:
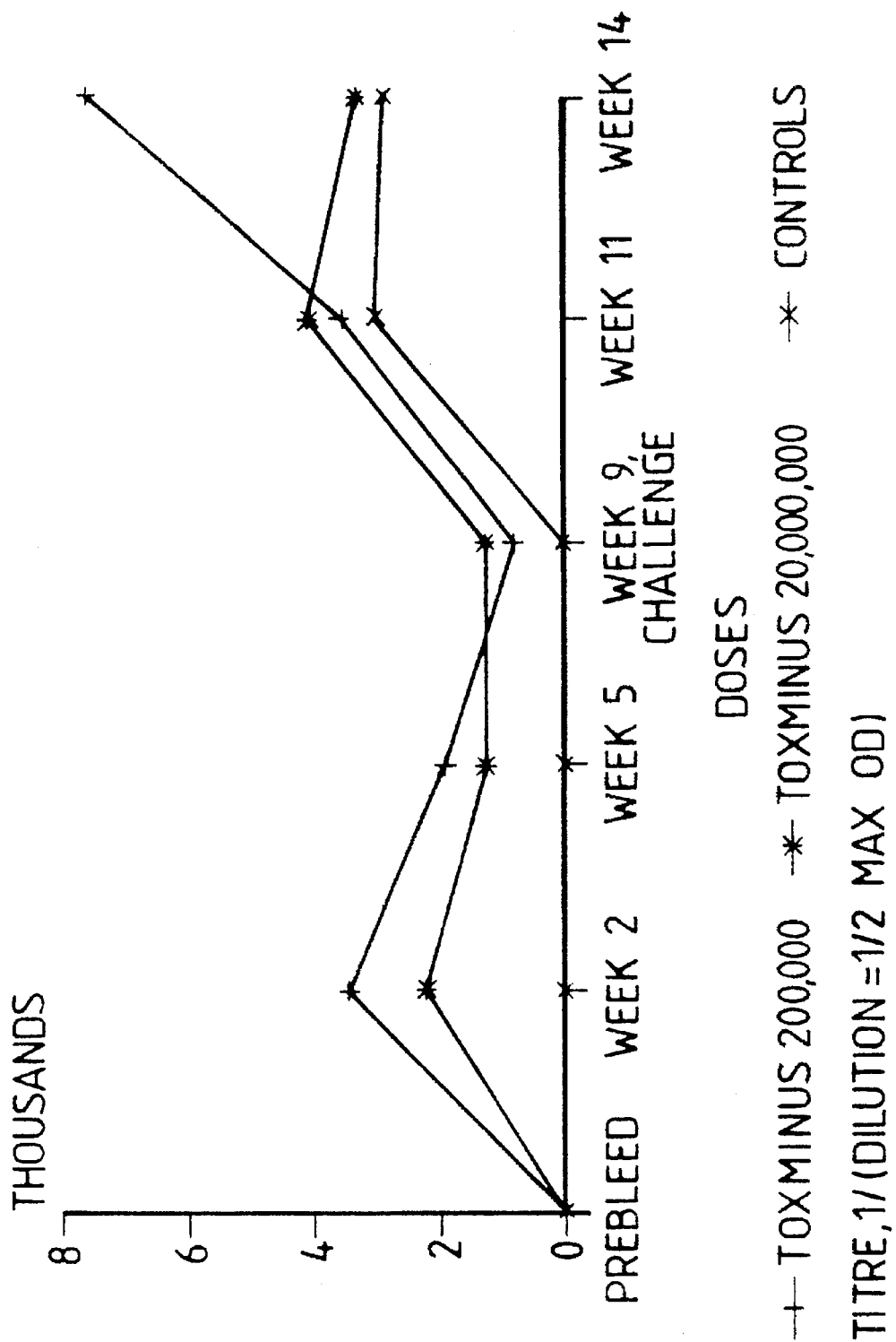
FIG. 5 is a graphical representation of the serological response of vaccinating sheep with varying doses of C. pseudotuberculosis Toxminus.

Serological results are shown in FIG. 5. Substantial titres are induced by the vaccination as per Example 3.

Post-mortem of the vaccinated animals inoculated with either $2×10^5$ or $2×10^7$ cfu of *C. pseudotuberculosis* Toxminus showed that there was no indication of infection or culturable vaccine strain present in the left (vaccinated) popliteal lymph node, or from any other tissue. The virulent strain used for challenge was recovered from all unvaccinated control animals, and from two of the 10 vaccinated sheep. Pathology results are shown in Table 3; except where noted, the virulent strain was cultured from all macroscopic lesions.

TABLE 3

| | Right challenge hind leg | | | | |
|---|---|---|---|---|---|
| | | | Vaccinates | | |
| Controls | | Toxminus $2 × 10^5$ | | Toxminus $2 × 10^7$ | |
| Pop. | SOI | Pop. | SOI | Pop. | SOI. |
| 2.5(4) | 0.5 | — | 1.0 | — | — |
| (Many) | 1.0 | — | — | — | — |
| 1.0(3) | 1.0 | — | — | — | 1.0 |
| 2.0 | — | — | — | 0.1 | — |
| (Many) | — | — | — | — | — |
| — | 0.5 | | | | |

Pop. = Popliteal Lymph node, SOI = Site of Inoculation {lesion size cm, (no. lesions)}

These data indicate that the PLD deleted *C. pseudotuberculosis* Toxminus strain confers resistance to challenge with virulent *C. pseudotuberculosis*, although this is not absolute at the challenge dose used.

REFERENCES:

1. Feinberg, A. P. and Volgelstein, B. 1983. A technique for radiolabelling DNA restriction endonuclease fragments to high specific activity. *Anal. Biochem.* 132: 66–13.
2. Hodgson, A. L. M., Bird, P. and Nisbet, I. T. 1990a. Cloning, nucleotide sequence and expression in *Escherichia coli* of the phospholipase D gene from *Corynebacterium pseudotuberculosis J. Bacteriol.* 172: 1256–1261.
3. Hodgson, A. L. M., Krywult, J. and Radford, A. J. 1990b. Nucleotide sequence of the erythromycin resistance gene from the Corynebacterium plasmid pNG2. *Nucleic Acids Res.* 18:1891.
4. Sambrook, J., Fritsch, E. F. and Manjarls, T. 1989. Molecular cloning: A laboratory manual, 2nd ed. Cold Spring Harbor Laboratory, Cold Spring Harbor, N.Y.

We claim:

1. A method for vaccinating an animal against virulent *Corynebacterium pseudotuberculosis* comprising administering to said animal a vaccination effective amount of living *Corynebacterium pseudotuberculosis* which is incapable of synthesizing phospholipase D.

2. A method according to claim 1 wherein the *Corynebacterium pseudotuberculosis* has a single or multiple nucleotide substitution, deletion and/or addition in a gene encoding phospholipase D.

3. The method according to claim 1 wherein the animal is a livestock animal.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 415 base pairs
        ( B ) TYPE: nucleic acid
        ( C ) STRANDEDNESS: single
        ( D ) TOPOLOGY: linear ( i i ) MOLECULE TYPE: DNA -5 region ( i i i ) HYPOTHETICAL: NO ( i v ) ANTI-SENSE: NO ( x i ) SEQUENCE DESCRIPTION: SEQ ID NO:1:

```
TTGTTATAGC GCGAGGTGGG GCCTAAAAGC CACGTTATAA AATCCTTCAT CTGTCTTTGA      60
TGCAGCGTCC CTGATCGCGT TGCTGTCGAC GATGCTCCGC ATCCCTTGCA TCTGTACCGG     120
GTCTTTCCTG TGGACGTTTT TGCCGTTCTT TTTTAGGAGA TTGCCGCAGA CGTTGCAGTG     180
ATTCCGGTAT GGATGTGAAG CCATAATCAA TAATTAGCAG CTTTAAATCT GCTATGGATA     240
CCCTAAAAGT TACAATTTTG GACACATTTT TTGTCCTTTA AGTTCAAAAA CCTTGAACGT     300
ATCTGACGCA TTTGAATACA TATCATTCAT ATGTAATGCC TGATTGATAA CGCCAACCTT     360
TTAAATGGGG CTCCCGCTCT CCTCTCTAGG GGATGGTTTT CTGTGTCAAC TGTCA         415
```

( 2 ) INFORMATION FOR SEQ ID NO:2:

( i ) SEQUENCE CHARACTERISTICS:
        ( A ) LENGTH: 584 base pairs
        ( B ) TYPE: nucleic acid
        ( C ) STRANDEDNESS: single
        ( D ) TOPOLOGY: linear ( i i ) MOLECULE TYPE: DNA -3 region ( i i i ) HYPOTHETICAL: NO ( i v ) ANTI-SENSE: NO ( x i ) SEQUENCE DESCRIPTION: SEQ ID NO:2:

```
CGTGGTGAGC TAGCAAATAA GTAGACATTT GACCGCTAGG CCTCTCAGCG TAAGAGGCCC      60
TAGCCCTGCA TCATAGCGAC GTTTGGCACT GGTAATTCGG TTGGAATGAC TACGAGTTGG     120
TCGTCGATAA GCATGGTGCG AACCGTGATA TTAAAAACTT CGGATATGAG TTCTGCGCTG     180
ATCACTTCCT GCGGGGAACC GGTAGCTACG ATGCTGCCAT TTTTCATAAC AATCAGGTGG     240
TCGGCGTACG GACAGCCTGT TGATAGTCGT GCAGTACCGC AGAACGGTGC GATTGAGCTG     300
AGTTGTAAGA GTCGTGCTAA CTCAAGAAGT TGGTACGGTG GGCGAGTCTA GGAAGGTGGT     360
GGGTTTCGTC CAGAAGTACC GTAGGAGTAT TTTGGGTCAG AACCATTGCA AGCCATACGT     420
GTCGACGCTG TCCACCGGAT AAATCGGTTC ACGTCGTTTG TGAGTGAGTT CTTTAACACT     480
GGCGGTCATT GAGAGCAGTC GTTCGACGGT CATCGAGTAT CTTCGGCGGT CCATTGATGT     540
AACCAATTGT GATGAGGGAA TCGTCCGCGG TCGGATCGTA GTCT                      584
```